United States Patent
Xie

(10) Patent No.: US 11,277,980 B2
(45) Date of Patent: Mar. 22, 2022

(54) PLANTING METHOD FOR MORELS

(71) Applicant: SICHUAN THREE POINT WATER BIOTECHNOLOGY CO., LTD., Mianyang (CN)

(72) Inventor: Linsen Xie, Mianyang (CN)

(73) Assignee: Sichuan Three Point Water Biotechnology Co Ltd

( * ) Notice: Subject to any disclaimer, the term of this patent is extended or adjusted under 35 U.S.C. 154(b) by 0 days.

(21) Appl. No.: 16/982,350

(22) PCT Filed: Jan. 22, 2019

(86) PCT No.: PCT/CN2019/072636
§ 371 (c)(1),
(2) Date: Sep. 18, 2020

(87) PCT Pub. No.: WO2019/179231
PCT Pub. Date: Sep. 26, 2019

(65) Prior Publication Data
US 2021/0029897 A1    Feb. 4, 2021

(30) Foreign Application Priority Data

Mar. 21, 2018   (CN) .......................... 201810235910.6

(51) Int. Cl.
*A01G 18/20* (2018.01)
*A01G 18/66* (2018.01)
(Continued)

(52) U.S. Cl.
CPC .............. *A01G 18/20* (2018.02); *A01C 14/00* (2013.01); *A01C 21/00* (2013.01); *A01D 91/02* (2013.01);
(Continued)

(58) Field of Classification Search
CPC ........ A01G 18/00; A01G 18/20; A01G 18/30; A01G 18/40; A01G 18/50; A01G 18/66;
(Continued)

(56) References Cited

U.S. PATENT DOCUMENTS 4,594,809 A * 6/1986 Ower et al. ............ A01G 18/00
47/1.1

FOREIGN PATENT DOCUMENTS

CN   104641929   * 11/2013   ............. A01G 18/00
CN   104956922      7/2015
(Continued)

OTHER PUBLICATIONS

"Artificial cultivation of true morels: current state, issues and perspectives", Liu et al., Critical Reviews in Biotechnology, 2017, downloaded from https://doi.org/10.1080/07388551.2017.1333082.*

(Continued)

*Primary Examiner* — Anne Marie Grunberg
(74) *Attorney, Agent, or Firm* — Timothy T. Wang; Ni, Wang & Massand, PLLC

(57) ABSTRACT

A planting method for morels is disclosed, including the following steps of: (1) preparing spawn; (2) flipping the spawn; (3) managing the humidity; and (4) fruiting for harvesting. The planting method is simple, is easy to learn and promote, has a high yield, and requires few spawn, thereby reducing planting costs and product costs.

5 Claims, 1 Drawing Sheet

(51) Int. Cl.

| | |
|---|---|
| *A01G 18/70* | (2018.01) |
| *A01G 18/40* | (2018.01) |
| *A01G 18/30* | (2018.01) |
| *A01G 18/50* | (2018.01) |
| *A01C 14/00* | (2006.01) |
| *A01C 21/00* | (2006.01) |
| *A01G 18/00* | (2018.01) |
| *A01D 91/02* | (2006.01) |
| *A01G 18/10* | (2018.01) |
| *A01G 18/22* | (2018.01) |
| *A01G 18/68* | (2018.01) |
| *A61K 36/062* | (2006.01) |
| *A61K 36/06* | (2006.01) |
| *A61K 36/00* | (2006.01) |
| *A01G 18/64* | (2018.01) |
| *A01G 11/00* | (2006.01) |

(52) U.S. Cl.
CPC .............. *A01G 11/00* (2013.01); *A01G 18/00* (2018.02); *A01G 18/10* (2018.02); *A01G 18/22* (2018.02); *A01G 18/30* (2018.02); *A01G 18/40* (2018.02); *A01G 18/50* (2018.02); *A01G 18/64* (2018.02); *A01G 18/66* (2018.02); *A01G 18/68* (2018.02); *A01G 18/70* (2018.02); *A61K 36/00* (2013.01); *A61K 36/06* (2013.01); *A61K 36/062* (2013.01)

(58) Field of Classification Search
CPC . A01G 18/70; A01G 1/04; A01G 1/00; A01G 18/10; A01G 18/22; A01G 18/64; A01G 18/68; A01G 11/00; C05D 1/02; C05B 7/00; C05C 9/00; C05F 11/00; C05G 3/00; C12N 1/14; Y02W 30/40; Y02W 30/43; A01H 15/00; A01D 91/02; A01C 14/00; A01C 21/00; A61K 36/00; A61K 36/06; A61K 36/062
USPC .............. 435/254.1, 71.1, 101, 105, 167, 88; 493/195, 932, 210; 424/93.5; 210/601; 71/5; 47/1.1, 59 S
See application file for complete search history.

(56) References Cited

FOREIGN PATENT DOCUMENTS

| CN | 104871819 A | * | 9/2015 | |
|---|---|---|---|---|
| CN | 105993590 | * | 5/2016 | ............. A01G 18/00 |
| CN | 106258478 | * | 1/2017 | ............... A01G 1/04 |
| CN | 106358751 | * | 2/2017 | ............... C05B 7/00 |
| CN | 106576901 | | 4/2017 | |
| CN | 107439221 | | 12/2017 | |
| CN | 107567954 | | 1/2018 | |
| CN | 105009935 | * | 7/2018 | ............. A01G 18/00 |
| WO | PCT/CN2019/072636 | | 9/2019 | |

OTHER PUBLICATIONS

Lieu et al, Critical Reviews in Biotechnology, 2017, downloaded from https://doi.org/10.1080/07388551.2017.1333082, Artificial cultivation of true morels: current state, issues and perspectives, pp. 1-13.*

Written opinion and search report for PCT/CN2019/072636, dated Sep. 26, 2019, Sichuan three point water biotechnology CO., LTD.—owned by Applicant.

* cited by examiner

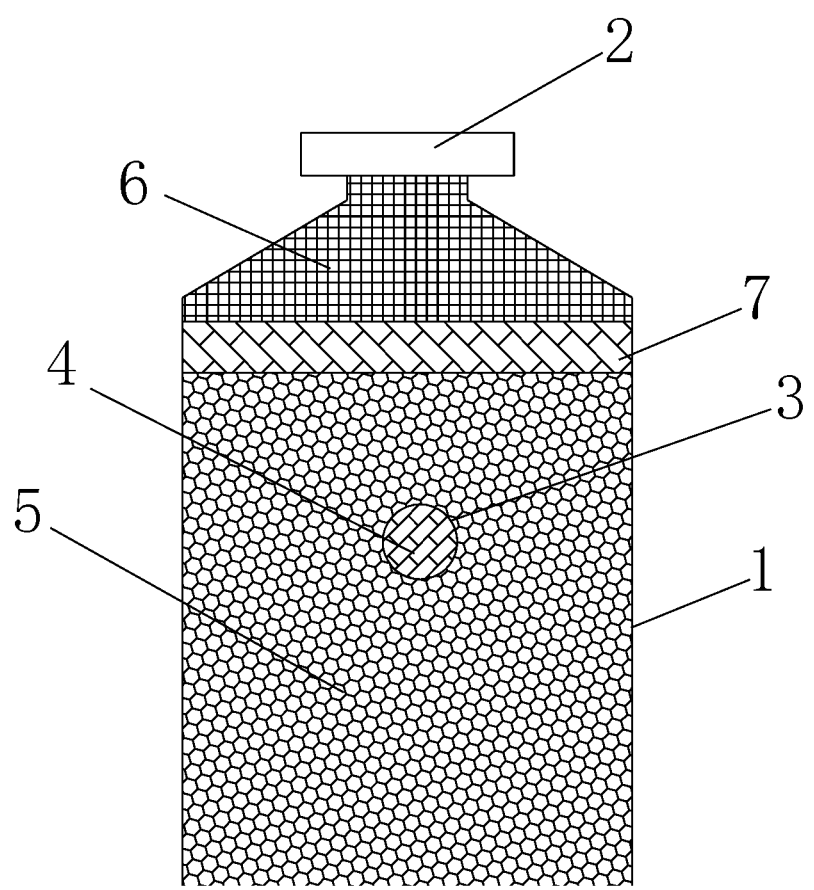

PLANTING METHOD FOR MORELS

CROSS REFERENCE TO RELATED APPLICATION

This application is a national stage entry from International Application No. PCT/CN2019/072636, filed Jan. 22, 2019, and claims the benefit of prior Application No. CN 201810235910.6, filed Mar. 21, 2018, each of which is hereby incorporated herein by reference in its entirety.

TECHNICAL FIELD

The disclosure relates to a planting method for wild mushroom, and in particular to a planting method for morels.

BACKGROUND

Morel is a rare edible fungus, named after a rugged and goat-tripe-like pileus thereof. Morel, also known as Morchella mushroom, sponge mushroom, or pinecone mushroom, is a rare edible and medicinal fungus for treating indigestion, qi stagnation, abdominal fullness and distention, and dyspnea with cough caused by accumulation of phlegm and qi counterflow.

The morel is the best-known delicious edible fungus among Ascomycetes, the pileus thereof contains seven essential amino acids to human body: isoleucine, leucine, lysine, methionine, phenylalanine, threonine, and valine. The morel is sweet in taste, cold in nature, and nontoxic. The fungus benefits intestines and stomach and regulates qi-flowing for eliminating phlegm.

Morels are fairly nutritious. It has been determined that a morel contains crude protein (20%), crude fat (26%), carbohydrates (38.1%), and a plurality of amino acids, and particularly glutamate content is as high as 1.76%. Therefore, morel is believed as "an extremely good protein source" and has a reputation of "meat of vegetarian diet". In the human body, proteins are composed of 20 amino acids; the morel includes 18 ones, eight of which cannot be produced in the human body but are especially important in human nutrition, known as "essential amino acids". In addition, it has been determined that there are at least eight vitamins in the morel: vitamins B1, B2 and B12, nicotinic acid, pantothenic acid, pyridoxine, biotin, folic acid, etc. The morel has nutrients comparable to milk, meat and fish meal. Therefore, the morel is often called one of "healthy foods" internationally. The morel contains tumor suppressor polysaccharides and antimicrobial and antiviral active components, which has immunopotentiating, antifatigue, antiviral, and tumor suppressor effects; Japanese scientists have found that morel extract contains a tyrosinase inhibitor that effectively inhibits the formation of lipofuscin. Rich selenium in the morel is a component of glutathione peroxidase in human red blood cell, which can transport a number of oxygen molecules to inhibit malignant tumors and inactivate cancer cells; on the other hand, antioxidation of vitamin E can be enhanced. The antioxidation of selenium can change the metabolic direction of carcinogens, and selenium binds to carcinogens for detoxification, thereby reducing or eliminating the risk of cancers.

The existing planting method for morels can be summarized in the following steps: preparing spawn, seeding the spawn, covering soil, preparing a mushroom spawn bag, mycelia coming up, placing the mushroom spawn bag, managing the humidity, removing the mushroom spawn bag, and fruiting. Specifically, well-mixed compost is bagged and sterilized under normal or high pressure, and then a spawn is inoculated in an aseptic environment; after dozens of days, mycelia are full of the bag, and then the bag is placed for 5-10 days to allow mycelia to penetrate the compost; well-cultured spawn is triturated and broadcast-spawned evenly in the field, and then 2-3 cm of soil is covered; after that, a perforated film is mulched optionally; the mushroom spawn bag is sterilized under normal or high pressure until mycelia grow all over the soil surface and appear white; after cooling and breaking, the mushroom spawn bag is placed on the ground; after a month, the mushroom spawn bag is removed until overgrowth; after managing the humidity, morels can fruit for harvesting.

The above planting method has the following defects:

1. The yield is unstable; the yield ranges from 0 to 800 catties, with an average yield of around 200 catties.
2. There are a number of planting steps and planting essentials, and these planting essentials are not easy to master; it is difficult to grasp the timing of placement of the mushroom spawn bag, i.e., early placement readily leads to undesired microbial infection, and late placement leads to low yield, and even no yield.

SUMMARY

To overcome defects that planting methods for morels have a number of steps and are difficult to grasp, with low and unstable yield, the disclosure provides a planting method for morels; the planting method is simple, is easy to learn and promote, has a stable and high yield, and requires few spawn, thereby reducing planting costs.

To solve the above technical problems, the disclosure adopts the following technical solutions:

A planting method for morels is provided, including the following steps:

step 1, preparing spawn 1.1 filling a mushroom spawn bag with compost, covering a layer of loose soil on the compost, and sealing the mushroom spawn bag for sterilization;

1.2 after sterilization, opening the mushroom spawn bag for inoculation, and going to the next step until morel mycelia grow down to at least 2-3 cm of the soil layer;

step 2, flipping the spawn cutting off the mushroom spawn bag, flipping on the ground directly, and compressing;

step 3, managing the humidity step 4, fruiting for harvesting.

In step 1.1, the soil layer is 1-2 cm thick.

In step 1.1, the compost is available from either those in the existing cultivation of morels, or those prepared by the following method: wheats are soaked in saturated limewater for one day, and then well-soaked corncobs and other components are mixed therein to prepare the compost.

In step 1.1, the mushroom spawn bag includes a body and a cap (an air-permeable bottle cap or a bottle cap for edible fungi), the cap is capped on the body, air holes are arranged at the side or bottom of the body, and a layer of air-permeable filter material is covered on the air holes. The mushroom spawn bag may also be made from a bag.

In step 1.1, the compost and the soil layer are needed to fill the entire mushroom spawn bag, and the compost is needed to be compressed.

In step 1.2, when inoculating, it is determined whether the mushroom spawn bag is inoculated in an aseptic environment according to the compactness thereof; after inoculation, the mushroom spawn bag is sealed. (If compact, the bag can be inoculated in the presence of microbes, because undesired microbes are difficult to penetrate the soil; if loose, the bag should be inoculated in an aseptic environment.)

In step 2, the spacing between mushroom spawn bags is 30-35 cm, surface soil is 16-25 cm thick, and a soil tank is 100-120 cm wide.

In step 2, the mushroom spawn bag is flipped on the ground and compressed, and mycelia grow up in a circular manner around the mushroom spawn bag.

In step 3 of managing the humidity, surface soil moisture is required at 70-85%.

In step 4, fruiting for harvesting is achieved 70-100 days after the mushroom spawn bag is flipped on the ground.

Such conditions as planting temperature and air humidity are subject to the existing planting requirements for morels.

Compared with the prior art, the disclosure has the following beneficial effects:

1. The planting method of the disclosure merely includes steps of preparing spawn, flipping the spawn, managing the humidity, and fruiting for harvesting. Planting steps of morels are substantially simplified, and mushroom spawn bags are flipped on the ground directly after inoculating the spawn. Because a soil layer is covered on the compost, and the soil functions as a barrier, morel mycelia will penetrate the soil into the compost directly, but other undesired fungi do not, so that undesired fungi do not contaminate easily and the yield will increase substantially. Unlike the existing planting methods, the disclosure does not need to take the good chance of the mushroom spawn bag, is easy to operate and grasp, and does not influence the yield stability due to operations by different people. Therefore, through the method provided by the disclosure, the yield is not only stable, but also increases substantially, which can reach at least 800 catties per mu. In the disclosure, it is important to cover the compost with a layer of soil, which can keep microbes out well; flipping the mushroom spawn bag on the ground is convenient for seeding; after inoculation, the spawn is not flipped until mycelia grow down to at least 2-3 cm of the soil layer, so as to fully ensure the inoculation quality of morels to facilitate subsequent seeding and yield improvement. In the disclosure, the mushroom spawn bag is cut off and flipped on the ground directly, so that mycelia in the mushroom spawn bag grow up in a circular manner and morels fruit in a circular and diffuse manner.

2. As required by the disclosure, the soil layer covering the compost is 1-2 cm thick; with this requirement of the thickness, the soil layer can achieve the objective of separating microbes, while allowing mycelia to penetrate the soil layer; if the soil layer is too thick or too thin, the yield stability and yield of morels will be influenced.

3. The mushroom spawn bag of the disclosure includes a body and a cap, the cap is capped on the body, air holes are arranged at the side or bottom of the body, and a layer of air-permeable filter material is covered on the air holes. The compost and the soil layer are needed to fill the entire mushroom spawn bag. Such structure of the mushroom spawn bag can play roles in improving the compactness of the mushroom spawn bag and separating microbes; air holes have air permeability.

4. As required by the disclosure, the surface soil moisture is 70-85%; this soil moisture contributes to the production of morels and the improvement of the yield of morels.

BRIEF DESCRIPTION OF THE DRAWINGS

FIG. 1 schematically illustrates the structure of a mushroom spawn bag of the disclosure.

In the drawing: 1 denotes a body, 2 denotes a cap, 3 denotes air holes, 4 denotes a layer of air-permeable filter material, 5 denotes compost, 6 denotes a soil layer, and 7 denotes mycelia.

DETAILED DESCRIPTION

The disclosure provides a planting method for morels, including the following steps:

step 1, preparing spawn 1.1 filling a mushroom spawn bag with compost 5, covering the compost 5 with a layer of loose soil 6, and sealing the mushroom spawn bag for sterilization, where the soil layer 6 is 1-2 cm thick, the mushroom spawn bag includes a body 1 and a cap 2, the cap 2 is capped on the body 1, air holes 3 are arranged at the side or bottom of the body 1, a layer of air-permeable filter material 4 is covered on the air holes 3, and the compost 5 and the soil layer 6 are needed to fill the entire mushroom spawn bag;

1.2 after sterilization, opening the mushroom spawn bag for inoculation, and going to the next step until morel mycelia 7 grow down to at least 2-3 cm of the soil layer;

step 2, flipping the spawn cutting off the mushroom spawn bag, flipping on the ground directly, and compressing, where the spacing between mushroom spawn bags is 30-35 cm, surface soil is 16-25 cm thick, a soil tank is 100-120 cm wide, and mycelia grow up in a circular manner around the mushroom spawn bag;

step 3, managing the humidity surface soil moisture is 70-85%;

step 4, fruiting for harvesting.

fruiting for harvesting 70-100 days after the mushroom spawn bag is flipped on the ground.

In step 1.1, the compost is available from either those in the existing cultivation of morels, or those prepared by the following method: wheats are soaked in saturated limewater for one day until the wheat expansion rate is no greater than 50%, and then well-soaked corncobs and other components are mixed therein to prepare the composts.

In step 1.2, when inoculating, it is determined whether the mushroom spawn bag is inoculated in an aseptic environment according to the compactness thereof; if compact, the bag can be inoculated in the presence of microbes; if loose, the bag should be inoculated in an aseptic environment; after inoculation, the mushroom spawn bag is capped and sealed.

The disclosure will be further described below in conjunction with examples, and the described examples are only a part of, not all of, the examples of the disclosure. All other examples obtained by persons of ordinary skill in the art based on the examples of the invention without creative efforts shall fall within the protection scope of the invention.

Example 1

A planting method for morels was provided, including the following steps:

step 1, preparing spawn 1.1 filling a mushroom spawn bag with compost, covering a layer of loose soil on the compost, and sealing the mushroom spawn bag for sterilization, where the soil layer was 1 cm thick, the mushroom spawn bag included a body and a cap, the cap was capped on the body, air holes were arranged at the side or bottom of the body, a layer of air-permeable filter material was covered on the air holes, and the compost and the soil layer were needed to fill the entire mushroom spawn bag;

1.2 after sterilization, opening the mushroom spawn bag for inoculation, and going to the next step until morel mycelia grew down to at least 2 cm of the soil layer;

step 2, flipping the spawn cutting off the mushroom spawn bag, flipping on the ground directly, and compressing, where the spacing between mushroom spawn bags was 30 cm, surface soil was 16 cm thick, a soil tank was 120 cm wide, and mycelia grew up in a circular manner around the mushroom spawn bag;

step 3, managing the humidity surface soil moisture was 70%;

step 4, fruiting for harvesting.

fruiting for harvesting 75 days after the mushroom spawn bag was flipped on the ground.

Example 2

A planting method for morels was provided, including the following steps:

step 1, preparing spawn 1.1 filling a mushroom spawn bag with compost, covering the compost with a layer of loose soil, and sealing the mushroom spawn bag for sterilization, where the soil layer was 1.5 cm thick, the mushroom spawn bag included a body and a cap, the cap was capped on the body, air holes were arranged at the side or bottom of the body, a layer of air-permeable filter material was covered on the air holes, and the compost and the soil layer were needed to fill the entire mushroom spawn bag;

1.2 after sterilization, opening the mushroom spawn bag for inoculation, and going to the next step until morel mycelia grew down to at least 2.5 cm of the soil layer;

step 2, flipping the spawn cutting off the mushroom spawn bag, flipping on the ground directly, and compressing;

step 3, managing the humidity surface soil moisture was 80%;

step 4, fruiting for harvesting.

fruiting for harvesting 70 days after the mushroom spawn bag was flipped on the ground.

Example 3

A planting method for morels was provided, including the following steps:

step 1, preparing spawn 1.1 filling a mushroom spawn bag with compost, covering the compost with a layer of loose soil, and sealing the mushroom spawn bag for sterilization, where the soil layer was 1.8 cm thick, the mushroom spawn bag included a body and a cap, the cap was capped on the body, air holes were arranged at the side or bottom of the body, a layer of air-permeable filter material was covered on the air holes, and the compost and the soil layer were needed to fill the entire mushroom spawn bag;

1.2 after sterilization, opening the mushroom spawn bag for inoculation, and going to the next step until morel mycelia grew down to at least 2.8 cm of the soil layer;

step 2, flipping the spawn cutting off the mushroom spawn bag, flipping on the ground directly, and compressing, where the spacing between mushroom spawn bags was 32 cm, surface soil was 20 cm thick, a soil tank was 110 cm wide, and mycelia grew up in a circular manner around the mushroom spawn bag;

step 3, managing the humidity surface soil moisture was 75%;

step 4, fruiting for harvesting.

fruiting for harvesting 87 days after the mushroom spawn bag was flipped on the ground.

Example 4

A planting method for morels was provided, including the following steps:

step 1, preparing spawn 1.1 filling a mushroom spawn bag with compost, covering a layer of loose soil on the compost, and sealing the mushroom spawn bag for sterilization, where the soil layer was 2 cm thick, the mushroom spawn bag included a body and a cap, the cap was capped on the body, air holes were arranged at the side or bottom of the body, a layer of air-permeable filter material was covered on the air holes, and the compost and the soil layer were needed to fill the entire mushroom spawn bag;

1.2 after sterilization, opening the mushroom spawn bag for inoculation, and going to the next step until morel mycelia grew down to at least 3 cm of the soil layer;

step 2, flipping the spawn cutting off the mushroom spawn bag, flipping on the ground directly, and compressing, where the spacing between mushroom spawn bags was 35 cm, surface soil was 18 cm thick, a soil tank was 100 cm wide, and mycelia grew up in a circular manner around the mushroom spawn bag;

step 3, managing the humidity surface soil moisture was 85%;

step 4, fruiting for harvesting.

fruiting for harvesting 93 days after the mushroom spawn bag was flipped on the ground.

Example 5

A planting method for morels was provided, including the following steps:

step 1, preparing spawn 1.1 filling a mushroom spawn bag with compost, covering the compost with a layer of loose soil, and sealing the mushroom spawn bag for sterilization, where the soil layer was 2 cm thick, the mushroom spawn bag included a body and a cap, the cap was capped on the body, air holes were arranged at the side or bottom of the body, a layer of air-permeable filter material was covered on the air holes, and the compost and the soil layer were needed to fill the entire mushroom spawn bag;

1.2 after sterilization, opening the mushroom spawn bag for inoculation, and going to the next step until morel mycelia grew down to at least 2 cm of the soil layer;

step 2, flipping the spawn cutting off the mushroom spawn bag, flipping on the ground directly, and compressing, where the spacing between mushroom spawn bags was 35 cm, surface soil was 16 cm thick, a soil tank was 118 cm wide, and mycelia grew up in a circular manner around the mushroom spawn bag;

step 3, managing the humidity surface soil moisture was 82%;

step 4, fruiting for harvesting.

fruiting for harvesting 100 days after the mushroom spawn bag was flipped on the ground.

Comparison of yields in all examples is shown in Table 1.

TABLE 1

| Comparison of yields in all examples | | |
| --- | --- | --- |
| Example | Planting area (mu) | Yield (catty) |
| Example 1 | 1 | 905 |
| Example 2 | 1 | 860 |
| Example 3 | 1 | 950 |
| Example 4 | 1 | 875 |
| Example 5 | 1.2 | 1,030 |

What is claimed is:

1. A planting method for morels, comprising:
preparing spawn, the preparing including
filling at least one mushroom spawn bag with compost, the at least one mushroom spawn bag having a top and a bottom;
covering the compost with a 1-2 cm layer of loose soil;
sealing the filled mushroom spawn bag for sterilization;
sterilizing the filled mushroom spawn bag;
after sterilization, opening the filled mushroom spawn bag for inoculation of the layer of loose soil with morel mycelia;
inoculating the layer of loose soil to grow the morel mycelia;
sealing the bag after the inoculating; and,
allowing the morel mycelia to grow 2-3 cm through the layer of loose soil and into the compost;
flipping the spawn, by flipping the filled mushroom spawn bag onto the ground for seeding, the flipping including
cutting off the top of the mushroom spawn bag to create an opening in the bag;
flipping the cut, and filled mushroom spawn bag onto the ground for seeding, the opening providing direct contact between the inoculated layer of soil and the ground; and
compressing the filled mushroom spawn bag onto the ground;
managing the humidity of the ground to have a surface soil moisture of 70-85%; and, harvesting the morels;
wherein the mushroom spawn bag comprises a body and a cap, the cap is capped on the body, air holes are arranged at the side or bottom of the body, and a layer of air-permeable filter material covers the air holes.

2. The planting method for morels according to claim 1, wherein the compost and the soil layer fill the entire mushroom spawn bag, and the compost is compressed.

3. The planting method for morels according to claim 1, wherein the method further comprises:
filling at least a second mushroom spawn bag with compost, the at least second mushroom spawn bag having a top and a bottom;
wherein the spacing between each mushroom spawn bag is 30-35 cm, and the surface soil of the ground is 16-25 cm thick.

4. The planting method for morels according to claim 1, wherein the mushroom spawn bag is flipped on the ground and compressed, and mycelia grow up in a circular manner around the mushroom spawn bag.

5. The planting method for morels according to claim 1, wherein the harvesting occurs 70-100 days after the mushroom spawn bag is flipped on the ground.

* * * * *